US012668895B2

(12) United States Patent
Liu et al.

(10) Patent No.: US 12,668,895 B2
(45) Date of Patent: Jun. 30, 2026

(54) YARN-OUT STATE DETECTION METHOD AND APPARATUS, DEVICE AND STORAGE MEDIUM

(71) Applicant: ZHEJIANG HENGYI PETROCHEMICAL CO., LTD., Hangzhou (CN)

(72) Inventors: Mingyi Liu, Zhejiang (CN); Xiantao Peng, Zhejiang (CN); Peng Wang, Zhejiang (CN); Xuan Wu, Zhejiang (CN); Dake Li, Zhejiang (CN); Feng Xu, Zhejiang (CN); Jianjun Sheng, Zhejiang (CN)

(73) Assignee: ZHEJIANG HENGYI PETROCHEMICAL CO., LTD., Hangzhou (CN)

( * ) Notice: Subject to any disclaimer, the term of this patent is extended or adjusted under 35 U.S.C. 154(b) by 24 days.

(21) Appl. No.: 18/807,602

(22) Filed: Aug. 16, 2024

(65) Prior Publication Data

US 2025/0207300 A1     Jun. 26, 2025

(30) Foreign Application Priority Data

Dec. 25, 2023    (CN) .......................... 202311806732.5

(51) Int. Cl.
   *D01H 13/32*      (2006.01)
   *G01N 21/88*      (2006.01)
                    (Continued)

(52) U.S. Cl.
   CPC ......... *D01H 13/32* (2013.01); *G01N 21/8851* (2013.01); *G01N 21/8915* (2013.01);
                    (Continued)

(58) Field of Classification Search
   CPC .......... B29C 54/582; B29C 2043/5891; B29C 2049/24308; B29C 2049/2071; B29C 45/842; B29C 45/768; B29C 2043/5833
   See application file for complete search history.

(56) References Cited

U.S. PATENT DOCUMENTS

| | | | |
|---|---|---|---|
| 5,615,014 A | 3/1997 | Okuda | |
| 2021/0118123 A1 | 4/2021 | Fang et al. | |
| 2023/0026193 A1 | 1/2023 | Baumgartinger et al. | |

FOREIGN PATENT DOCUMENTS

| | | |
|---|---|---|
| CN | 106596568 A | 4/2017 |
| CN | 109493327 A | 3/2019 |

(Continued)

OTHER PUBLICATIONS

First Office Action and Search Report received in CN 202311806732.5 dated Feb. 2, 2024.

(Continued)

*Primary Examiner* — Stella K Yi
(74) *Attorney, Agent, or Firm* — Knobbe, Martens, Olson & Bear, LLP

(57)            ABSTRACT

Provided is a yarn-out state detection method, an electronic device and a storage medium, relating to the field of computer, and in particular to the fields of detection technology, artificial intelligence technology and neural network model technology. The method includes: collecting a first image and laser reflection data of a target yarn path in a spinning box; obtaining an image feature of the target yarn path according to the first image; obtaining a laser feature of the target yarn path according to the laser reflection data; and using a yarn-out state detection model to obtain a yarn-out state of the target yarn path according to the image feature and the laser feature.

7 Claims, 6 Drawing Sheets

(51) Int. Cl.
   *G01N 21/89*       (2006.01)
   *G01N 33/36*       (2006.01)
(52) U.S. Cl.
   CPC ... *G01N 33/365* (2013.01); *G01N 2021/8883*
   (2013.01); *G01N 2021/8887* (2013.01)

(56)          References Cited

FOREIGN PATENT DOCUMENTS

| | | | |
|---|---|---|---|
| CN | 110175659 | A | 8/2019 |
| CN | 110308147 | A | 10/2019 |
| CN | 110992343 | A | 4/2020 |
| CN | 210775245 | U | 6/2020 |
| CN | 112111824 | A | 12/2020 |
| CN | 112505051 | A | 3/2021 |
| CN | 116934308 | A | 10/2023 |
| CN | 116993710 | A | 11/2023 |
| CN | 117115135 | A | 11/2023 |
| CN | 117197087 | A | 12/2023 |

OTHER PUBLICATIONS

Notification to Grant Patent Right for Invention and Search Report in CN 202311806732.5 dated Feb. 5, 2024.

Lyu et al., Operational Modal Analysis of a Rotating Structure Subject to Random Excitation Using a Tracking Continuously Scanning Laser Doppler Vibrometer via an improved Demodulation Method, Journal of Vibration and Acoustics, vol. 144, dated Feb. 2022.

Lin et al., Research on Chalky Rice Detection Based on Visible Spectrogram and Deep Neural Network Technology, Spectroscopy and Spectral Analysis, vol. 40, No. 1, pp. 233-238, dated Jan. 2020.

Extended European Search Report issued in EP Application No. 24195043.5, dated Feb. 24, 2025.

Office Action issued in Japanese Application No. 2024-225150, dated Feb. 18, 2025.

First Office Action and Search Report received in CN 202311806732.5 dated Feb. 6, 2024.

Notification to Grant Patent Right for Invention and Search Report in CN 202311806732.5 dated Mar. 4, 2024.

First sliding window          Second sliding window

YARN-OUT STATE DETECTION METHOD AND APPARATUS, DEVICE AND STORAGE MEDIUM

CROSS-REFERENCE TO RELATED APPLICATIONS

The present application claims priority to Chinese Patent Application No. CN202311806732.5, filed with the China National Intellectual Property Administration on Dec. 25, 2023, the disclosure of which is hereby incorporated herein by reference in its entirety.

TECHNICAL FIELD

The present disclosure relates to the field of computer, and in particular to the fields of detection technology, artificial intelligence technology, neural network model technology and model training technology.

BACKGROUND

In the chemical fiber industry, the speed at which the melt spinning box produces yarns is very fast. In addition, the fiber yarns extruded from the spinneret plate are extremely thin and visually appear as strip-shaped phantoms. It is difficult to accurately confirm the state of the yarns visually in the prior art. The quality of the yarns can only be ensured by shoveling and cleaning the spinneret plate after abnormal situations such as broken yarn and floating yarn occur or at a fixed period.

SUMMARY

The present disclosure provides a yarn-out state detection method and apparatus, a device and a storage medium, to solve or alleviate one or more technical problems in the prior art.

In a first aspect, the present disclosure provides a yarn-out state detection method, including:

collecting a first image and laser reflection data of a target yarn path in a spinning box;

obtaining an image feature of the target yarn path according to the first image;

obtaining a laser feature of the target yarn path according to the laser reflection data; and using a yarn-out state detection model to obtain a yarn-out state of the target yarn path according to the image feature and the laser feature.

In a second aspect, the present disclosure provides a yarn-out state detection apparatus, including:

a collecting module configured to collect a first image and laser reflection data of a target yarn path in a spinning box;

an image feature determining module configured to obtain an image feature of the target yarn path according to the first image;

a laser feature determining module configured to obtain a laser feature of the target yarn path according to the laser reflection data; and a detection module configured to use a yarn-out state detection model to obtain a yarn-out state of the target yarn path according to the image feature and the laser feature.

In a third aspect, provided is a method for training a yarn-out state detection model, including:

obtaining a training image feature of a target yarn path according to a sample image of the target yarn path;

obtaining a training laser feature of the target yarn path according to laser sample data of the target yarn path;

using a first detection model to obtain a predicted result of a yarn-out state of the target yarn path according to the training image feature and the training laser feature;

determining a loss function according to the predicted result and an actual result of the yarn-out state of the target yarn path; and updating a parameter of the first detection model based on the loss function to obtain a trained yarn-out state detection model.

In a fourth aspect, provided is an apparatus for training a yarn-out state detection model, including:

an image feature extraction module configured to obtain a training image feature of a target yarn path according to a sample image of the target yarn path;

a laser feature extraction module configured to obtain a training laser feature of the target yarn path according to laser sample data of the target yarn path;

a prediction module configured to use a first detection model to obtain a predicted result of a yarn-out state of the target yarn path according to the training image feature and the training laser feature;

a loss function determining module configured to determine a loss function according to the predicted result and an actual result of the yarn-out state of the target yarn path; and a training module configured to update a parameter of the first detection model based on the loss function to obtain a trained yarn-out state detection model.

In a fifth aspect, provided is an electronic device, including:

at least one processor; and a memory connected in communication with the at least one processor;

where the memory stores an instruction executable by the at least one processor, and the instruction, when executed by the at least one processor, enables the at least one processor to execute the method of any embodiment of the present disclosure.

In a sixth aspect, provided is a non-transitory computer-readable storage medium storing a computer instruction thereon, and the computer instruction is used to cause a computer to execute the method according to any one of the embodiments of the present disclosure.

The beneficial effects of the technical solution provided in the present disclosure at least include:

The comprehensive application of the image processing and laser scanning technologies can effectively improve the accuracy and efficiency of the yarn state detection. At the same time, the use of the advanced machine learning method can make the system have the better adaptability and intelligence and detect the abnormal state in advance, improving the stability of the entire spinning process and the product quality.

It should be understood that the content described in this part is not intended to identify critical or essential features of embodiments of the present disclosure, nor is it used to limit the scope of the present disclosure. Other features of the present disclosure will be easily understood through the following description.

BRIEF DESCRIPTION OF THE DRAWINGS

In the accompanying drawings, the same reference numbers represent the same or similar parts or elements throughout the accompanying drawings, unless otherwise specified. These accompanying drawings are not necessarily drawn to scale. It should be understood that these accompanying drawings only depict some embodiments provided according to the present disclosure, and should not be considered as limiting the scope of the present disclosure.

DETAILED DESCRIPTION

The present disclosure will be described below in detail with reference to the accompanying drawings. The same reference numbers in the accompanying drawings represent elements with identical or similar functions. Although various aspects of the embodiments are shown in the accompanying drawings, the accompanying drawings are not necessarily drawn to scale unless specifically indicated.

In addition, in order to better illustrate the present disclosure, numerous specific details are given in the following specific implementations. Those having ordinary skill in the art should understand that the present disclosure may be performed without certain specific details. In some examples, methods, means, elements and circuits well known to those having ordinary skill in the art are not described in detail, in order to highlight the subject matter of the present disclosure.

In the related art, the polyester melt is extruded from a spinneret plate and then cooled and solidified to form nascent fibers, and the nascent fibers are oiled and bundled through an oil nozzle and then sent to a winding machine through a yarn guide hook for winding and forming. After a period of operation, the residual polyester material will gradually accumulate around a yarn outlet hole of the spinneret plate. The residual polyester material will block the yarn outlet hole after hardened, which may change the cross-sectional shape of the melt stream, cause scratches on the fiber yarns, and result in thinning, floating and end breakage of the yarns. The traditional practice is to shovel and clean the spinneret plate at a fixed period to ensure the cleanliness of each yarn outlet hole on the spinneret plate. This regular maintenance strategy lacks flexibility, and may be too frequent to thereby waste resources and time in some cases or not frequent enough in some cases. Once the yarn breaks, the entire yarn spindle will be scrapped.

Due to the extremely fast speed of the yarn output of a spinning box, the state of the yarn is difficult to be accurately captured. The blur caused by this high-speed motion not only affects the image quality, but also reduces the accuracy of fault detection. The fault can only be found visually in the case of obvious abnormality such as floating yarn or broken yarn in the prior art.

In order to at least partially solve one or more of the above-mentioned problems and other potential problems, an embodiment of the present disclosure provides a yarn-out state detection method, which combines visual detection and laser scanning, and enhances the image data and laser reflection data through an algorithm to accurately detect the yarn-out state. The use of the technical solution of the disclosed embodiment can effectively improve the accuracy and efficiency of the yarn state detection, detect the abnormal state in advance, and improve the stability of the entire spinning process and the product quality.

Figure 1:
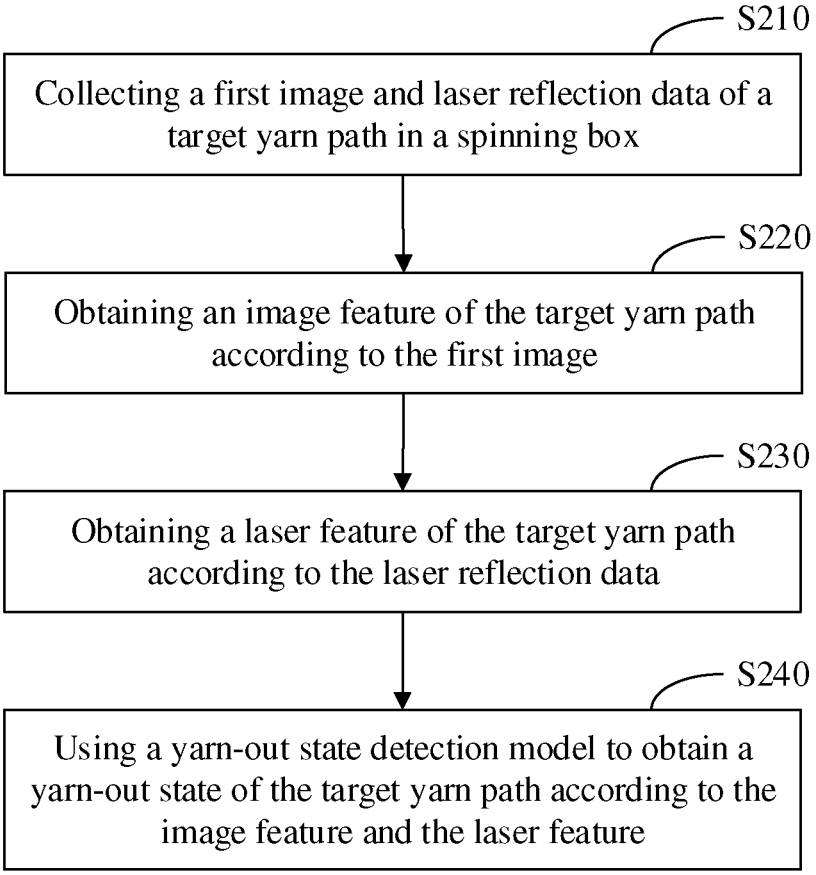
FIG. 1 is a schematic flow chart of a yarn-out state detection method according to an embodiment of the present disclosure.

FIG. 1 is a schematic flow chart of a yarn-out state detection method according to an embodiment of the present disclosure. As shown in FIG. 1, the method includes at least the following steps:

S210: collecting a first image and laser reflection data of a target yarn path in a spinning box.

Figure 2:
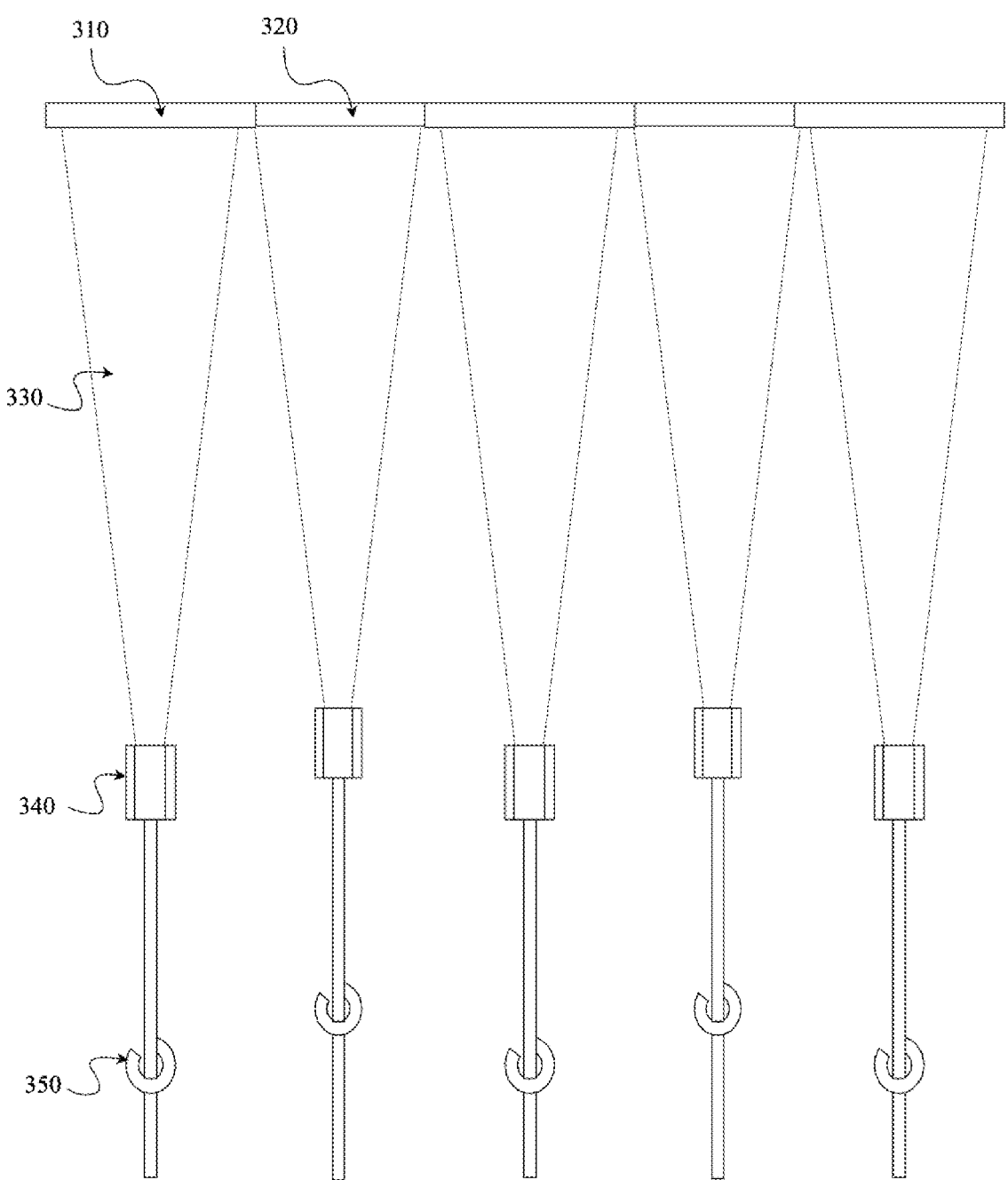
FIG. 2 is a structural schematic diagram of a plurality of yarn paths according to an embodiment of the present disclosure.

In an embodiment of the present disclosure, the spinning box has a plurality of spinneret plates and the same number of yarn paths, and the yarn path may be understood as a moving path of a group of fiber yarn bundles corresponding to each spinneret plate. Specifically, as shown in FIG. 2, three first spinneret plates 310 are located in the front row, and two second spinneret plates 320 are located in the back row. The yarn path refers to a moving path of fiber yarn bundles that can be directly observed in the process in which a group of fiber yarns 330 extruded from a spinneret plate are oiled and bundled through an oil nozzle 340 and then enter a spinning tunnel through a yarn guide hook 350. It is inconvenient to observe after entering the spinning tunnel. The fiber yarns 330 are in a ghost shape before being bundled. It should be noted that the yarn guide hooks may include an upper yarn guide hook and a lower yarn guide hook, and the upper yarn guide hook is located above the oil nozzle.

The first image of the target yarn path refers to an image obtained by photographing at least one yarn path through a camera device. It is possible to shoot a plurality of yarn paths at one time and then cut out the first image of the target yarn path. It is also possible to shoot each target yarn path separately to obtain the better image quality and better shooting angle. The camera device may be a high-speed camera that uses the high-speed photography technology to capture images of yarn paths. The high-speed camera can capture images at a very high frame rate, thus reducing or eliminating artifacts caused by rapid motion of yarn bundles. The visibility of the yarn state can be improved through proper lighting and shooting angle.

The laser reflection data refers to the reflection signal data obtained after using the laser scanning technology to irradiate the yarn bundle in the target yarn path. When the laser beam hits the moving yarn, the laser beam will be scattered, reflected or refracted. The signals generated by these optical interactions can provide the important information about the yarn. The collected reflection signal data is processed algorithmically to extract a key parameter about the yarn state.

S220: obtaining an image feature of the target yarn path according to the first image.

The image features of the yarns, such as the width, shape and bundle spacing of the yarns, on the target yarn path may be extracted from the first image using image processing algorithms (such as edge detection and contrast enhancement).

S230: obtaining a laser feature of the target yarn path according to the laser reflection data.

The laser features (such as diameter, speed and surface roughness) of the target yarn path and the optical properties generated by laser scattering and reflection may be obtained by performing feature extraction on the laser reflection data. The diameter and surface condition of the yarn may be inferred by analyzing the distribution of reflection intensity.

S240: using a yarn-out state detection model to obtain a yarn-out state of the target yarn path according to the image feature and the laser feature.

The pre-trained machine learning or deep learning model (such as convolutional neural network, support vector machine, etc.) is used to process the image feature and laser feature, so as to output the yarn-out state of the yarn path. In one example, the yarn-out state detection model may be a Convolutional Neural Network (CNN) model because it is good at processing the image data and can provide detailed prediction through probabilistic output.

The yarn-out state may include a plurality of state categories defined according to different conditions and risk levels that may occur in the yarns. These state categories not only describe the current condition of the yarns, but also hint at the risk level that may lead to yarn breakage. A group of example states are as follows:

State 1—Normal:
  Description: The yarn runs normally with no visible anomalies.
  Risk level: Low. There is almost no risk of yarn breakage.
State 2—Slight Fluctuation:
  Description: The yarn shows slight fluctuation or vibration but not beyond the normal range.
  Risk level: Low to medium. It may indicate that the machine operating condition needs to be slightly adjusted.
State 3—Obvious Fluctuation:
  Description: The yarn fluctuates obviously, which may affect the yarn quality.
  Risk level: Medium. The long-term operation may cause the quality problem or yarn breakage with a small probability.
State 4—Distorted:
  Description: The yarn surface appears distorted or rough, and the running path of the yarn is irregular.
  Risk level: Medium to high. This situation is more likely to cause yarn breakage or cessation of production.
State 5—Tension Anomaly:
  Description: The tension of the yarn is significantly abnormal and may appear too loose or too tight.
  Risk level: High. This may cause yarn breakage.
State 6—Obvious Damage:
  Description: The yarn shows obvious physical damage, such as wear, sign of breakage, etc.
  Risk level: Very high. It is very likely to immediately cause yarn breakage or a serious product quality problem.

After the detection result of the yarn-out state is obtained, the shoveling operation of the spinning box corresponding to the yarn path with a higher risk level may be further arranged in time according to the personnel situation and production rhythm.

According to the solution in the embodiment of the present disclosure, the comprehensive application of the image processing and laser scanning technologies can effectively improve the accuracy and efficiency of the yarn state detection. At the same time, the use of the advanced machine learning method can make the system have the better adaptability and intelligence and detect the abnormal state in advance, improving the stability of the entire spinning process and the product quality.

In a possible implementation, S210 of collecting the first image and the laser reflection data of the target yarn path in the spinning box further includes the steps of:

S211: controlling an inspection equipment to move to be in front of a spinning box to be detected.

In an embodiment of the present disclosure, the inspection equipment may be an AGV (Automated Guided Vehicle) that runs according to a preset route or instruction, or may be an inspection equipment that moves on a fixed track, which is not limited here. The advantage of using the inspection equipment is that a set of collection equipment can be used to detect a plurality of spinning boxes in a plurality of adjacent channels one by one, and at the same time, the movable inspection equipment can adjust the shooting angle to facilitate collection of the detection data with better quality.

S212: triggering a camera device and a laser scanning device of the inspection equipment to simultaneously collect the first image and the laser reflection data of the target yarn path in the spinning box, where the target yarn path includes a moving path formed by converging a plurality of yarn bundles ejected from a spinneret plate into one strand through a yarn guide hook.

In an embodiment of the present disclosure, a plurality of detection stations may be preset in front of the spinning box, to prevent the yarn paths in the front row from blocking the yarn paths in the rear row, and to facilitate shooting the yarn paths at different positions in the rear row at a suitable angle. In other words, each detection station can be used to collect data of a plurality of yarn paths. After arriving at a detection station, the yarn paths corresponding to this detection station are regarded as a plurality of target yarn paths, and the camera device and laser scanning device of the inspection equipment are triggered to collect the first image and laser reflection data for each target yarn path in turn.

According to the solution in the embodiment of the present disclosure, the movable inspection equipment is used to collect the data of the target yarn path at a plurality of detection stations, and can collect the detection data with better quality.

In a possible implementation, S220 of obtaining the image feature of the target yarn path according to the first image further includes the steps of:

S221: performing morphological processing on the first image to obtain a second image.

S222: obtaining the image feature of the target yarn path according to the second image.

In an embodiment of the present disclosure, the morphological transformation (such as erosion and dilation) is used to improve the image structure of the yarns, so that the yarn state feature in the obtained second image is more easily recognized by the model.

In a possible implementation, S221 of performing morphological processing on the first image to obtain the second image further includes the steps of:

using a first sliding window to traverse the first image, and performing a dilation operation to obtain a dilated image during each slide;

using a second sliding window to traverse the first image, and performing an erosion operation to obtain an eroded image during each slide; and obtaining the second image according to morphological gradients of the dilated image and the eroded image.

In an embodiment of the present disclosure, the dilation operation is a morphological operation, and has the effect of enlarging objects in an image. Specifically, a structure element may be moved as a sliding window over the image. If the structure element overlaps any part of an object (yarn), a pixel is added at the center of the structure element. The result is that the boundaries of the objects are expanded outwards, highlighting the larger structures.

The erosion is an operation opposite to the dilation, and has the effect of reducing objects in an image. The "sliding window" is also used, but the rule is that the center pixel of the window remains unchanged only if all pixels within the window are part of objects. The result is that the boundaries of the objects are reduced inwards, and details and small objects may be eliminated.

The morphological gradient is calculated by subtracting the eroded image from the dilated image. Since the dilation enlarges the edges of objects and the erosion reduces the edges of objects, the difference between them emphasizes these edges. This method is particularly applicable to highlight thin lines and details, such as fiber edges in a yarn image.

According to the solution of the embodiment of the present disclosure, the application of the morphological gradient in the yarn image can make the edges of the yarns clearer and more obvious. This is very helpful for subsequent feature extraction and model prediction because the clearer yarn outline is provided, making it easier for the algorithm to distinguish between yarns and background. This edge enhancement technology is particularly useful for processing the yarn images produced under high-speed motion or low-contrast condition, and enhances the ability of the model to recognize the yarn state.

In a possible implementation, the first sliding window and the second sliding window use different structure elements, and the neighborhood and shape of the structure element (or kernel) depend on a specific feature desired to be extracted or emphasized from the image. After being extruded from the spinneret plate, the fiber yarn bundles gradually gather into one bundle from top to bottom, that is, the yarn path is approximately vertical. During morphological processing, the thickness and the surface roughness of the yarn should be highlighted. For this purpose, the structure elements used for erosion and dilation need to be designed according to the specific characteristics of the yarn. Considering that the yarn is approximately vertical and the flight feather and rough edge in the horizontal direction need to be emphasized, the structure elements may be designed using the following strategy:

For the eroded structure element, in order to emphasize the longitudinal characteristics of the yarn and reduce the influence of the rough edge, a rectangular structure element that is longer in the vertical direction may be used. In terms of size, the height of the structure element should be greater than the width thereof, so that the horizontal features of the yarn can be more affected during erosion. The resulting structure element will remove small horizontal projections from the yarn edge during erosion, thus helping to reduce the influence of the rough edge.

For the dilated structure element, a similar rectangular structure element may be used. In order to restore the longitudinal information of the yarn lost due to erosion, the dilated structure element may be slightly wider, but still remain longer in the vertical direction. The resulting structure element will help restore the original thickness of the yarn during dilation while avoiding excessive amplification of the rough edge in the horizontal direction.

Figure 3:
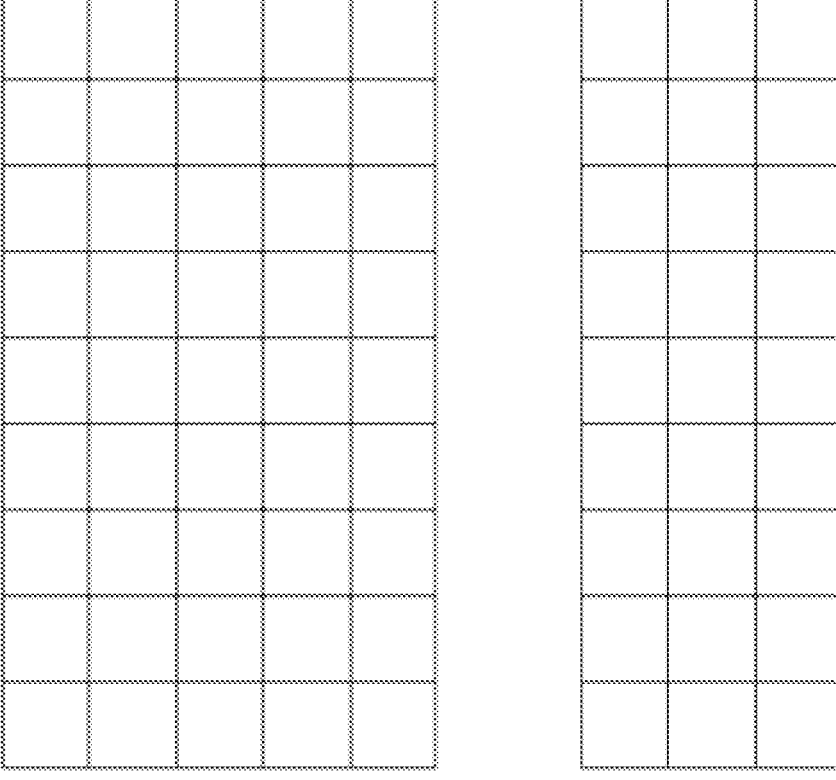
FIG. 3 is a structural schematic diagram of a sliding window according to an embodiment of the present disclosure.

In a specific example, the first sliding window is a rectangular structure element with an aspect ratio of 3 to 5:2, and the second sliding window is a rectangular structure element with an aspect ratio of 2 to 5:1. For example, as shown in FIG. 3, the first sliding window has a length of 9*X pixels and a width of 5*X pixels, and the second sliding window has a length of 9*X pixels and a width of 3*X pixels. For both of them, the vertical direction is the long edge direction, and X is a positive integer greater than 0.

In another example, the first sliding window is an inverted trapezoidal structure element with an aspect ratio of 3 to 5:2 that is wide at the top and narrow at the bottom, and a ratio of the upper width to the lower width is 1.1 to 1.3:1. The second sliding window is an inverted trapezoidal structure element with an aspect ratio of 2 to 5:1, and a ratio of the upper width to the lower width is 1.1 to 1.3:1. The inverted trapezoidal structure is used to provide a shape close to the yarn path, which is wide at the top and narrow at the bottom.

It should be noted that the selection of structure elements needs to be adjusted according to the specific application scenario and the expected result. Tests may be required to determine the optimal size and shape.

According to the solution in the embodiment of the present disclosure, the structure elements designed in the above manner can effectively highlight the thickness and surface roughness of the yarn while reducing the influence of the rough edge in the horizontal direction. Such customized structure element design is a key part of morphological processing and can significantly improve the effect of yarn image processing.

In a possible implementation, S222 of obtaining the image feature of the target yarn path according to the second image further includes the steps of:

S222-1: dividing the second image into a plurality of segments in a length direction of the target yarn path to obtain a plurality of sub-images.

S222-2: performing feature extraction on the plurality of sub-images to obtain a plurality of first image features.

S222-3: obtaining the image feature of the target yarn path according to the plurality of first image features and corresponding weight values.

In the embodiment of the present disclosure, since the yarn paths gradually converge and narrow from top to bottom and eventually gather into one strand, the closer the fiber yarn bundles get to the bottom, the smaller the spacing between the fiber yarn bundles, making it more difficult to accurately identify the thickness and surface roughness of each yarn bundle. Therefore, the weight values from high to low may be set sequentially for the first image features corresponding to the sub-images along the direction of the yarn path. That is, the higher weight values are assigned to the first image features extracted from several sub-images at the upper part of the yarn path, and the weight values of the first image features extracted from the sub-images at the lower part of the yarn path are reduced.

According to the solution in the embodiment of the present disclosure, the corresponding weight value are assigned to the first image feature extracted from each sub-image according to the morphological feature of the yarn path, so that the model is convenient for paying more attention to the image features of the upper area of the yarn path.

In the laser scanning detection, the yarns in different yarn-out states will show some obvious differences in the laser reflection or scattering data. These differences are mainly due to changes in physical properties and motion states of the yarns, and specifically includes:

(1) Yarn diameter: the diameters of yarns in different specifications may be different, and the micropore apertures of the spinneret plates used are different. For example, the yarn in the normal state should have the uniform diameter, but the diameter of the yarn may change abnormally as the yarn outlet hole is gradually blocked.

(2) Surface roughness: the yarn in the normal state usually has a relatively smooth surface, while the problematic yarn may show a higher surface roughness, which will affect the scattering pattern of the laser beam.

(3) Scattering intensity: the scattering intensity will change with the change of the surface characteristic of the yarn. The scattering signal from a smooth surface is relatively weak and uniform, while a rough or irregular surface may lead to an enhanced scattering signal and a change in pattern.

(4) Scattering angle: when the yarns in different states are scanned by laser, the scattering angles may be different due to differences in surface characteristic and shape. For example, the scattering angle of the normal yarn may be relatively stable, while the scattering angle of the abnormal yarn (for example, the surface is rough or the cross-section shape is changed) may be irregular.

(5) Spectral characteristic: the spectral characteristic produced when the laser interacts with the yarn may also vary depending on the state of the yarn. Different physical states may lead to slight changes in the laser spectrum.

(6) Continuity of reflected light beam: the reflection of the normal yarn under laser scanning should be continuous and uniform, while the discontinuous yarn may cause interruption or irregularity of reflection.

In summary, the abnormal features of fibers can be effectively identified and distinguished by analyzing the differences in the laser scanning data, thus providing important information for monitoring and quality control of the spinning process.

In a possible implementation, S222-3 of obtaining the image feature of the target yarn path according to the plurality of first image features and corresponding weight values further includes the steps of:

determining weight values of the plurality of sub-images according to width values of yarn paths contained in the plurality of sub-images;

obtaining second image features of the plurality of sub-images according to the weight values of the plurality of sub-images and the first image features; and obtaining the image feature of the target yarn path according to the second image features of the plurality of sub-images.

In the embodiment of the present disclosure, a corresponding weight value may be set according to the width value of the yarn path in each sub-image. The width value may be the maximum width, minimum width or average width. After the first image feature is multiplied by the weight value, the second image feature is obtained. Then the second image features of the plurality of sub-images are synthesized to finally obtain the image feature of the target yarn path.

In a possible implementation, S230 of obtaining the laser feature of the target yarn path according to the laser reflection data further includes the steps of:

S231: performing short-time Fourier transform on the laser reflection data to obtain a time-frequency representation result.

In the embodiment of the present disclosure, the Short-Time Fourier Transform (STFT) is performed on the laser reflection data, the sliding windows are applied to signals, and then the Fourier transform is performed on a signal in each window to thereby obtain a time-frequency representation of the signal, ensuring the time locality, and allowing observation of the frequency component of the signal that varies over time.

S232: determining a time-frequency feature according to the time-frequency representation result.

The result of the STFT, namely a time-frequency graph, is used to analyze the time-frequency feature of the laser reflection data. The time-frequency graph shows the changes of different frequency components in the signal over time, and provides the frequency information of the signal at different time points. The time-frequency features that need to be identified specifically include:

The distribution of frequency components in the time-frequency graph is identified, including: seeing which frequencies are dominant in the signal and how those frequencies change over time. For example, the significance of certain frequencies in the laser scan data of the yarn may indicate specific physical states or changes.

The energy distribution is analyzed, and the energy of frequency components at different time points is evaluated. The areas with higher energy usually appear as brighter areas in the time-frequency graph. The energy distribution can reveal the dynamic characteristic of the signal, such as the stability of the yarn or the emergence of the abnormal state.

The time change is observed and the changes of the frequency components over time are noted. For example, a sudden change in frequency may indicate a change in the yarn state or some abnormality.

S233: obtaining the laser feature of the target yarn path according to the time-frequency feature.

In the embodiment of the present disclosure, the time-frequency feature obtained from the time-frequency graph is further operated and analyzed to extract the key information and obtain the laser feature of the target yarn path, specifically including: identifying an energy peak within a specific frequency range, calculating the durations of different frequency components, etc.

According to the solution in the embodiment of the present disclosure, the rich information can be extracted from the time-frequency graph, helping to accurately identify the behavior and state of the yarn during the laser scanning process to achieve quality control.

In a possible implementation, S233 of obtaining the laser feature of the target yarn path according to the time-frequency feature further includes the steps of:

extracting a main frequency feature, an energy peak feature and a dynamic change feature from the time-frequency feature; and obtaining the laser feature of the target yarn path according to the main frequency feature, the energy peak feature and the dynamic change feature.

In the embodiment of the present disclosure, the feature extraction is further performed on the time-frequency feature, so that the extracted feature should capture the key attribute of the signal. The specific steps include:

extracting the main frequency components, and determining the specific values of the main frequencies and the durations and intensities thereof in the entire signal;

identifying an energy peak in the time-frequency graph, where the energy peak indicates that the signal strength is particularly high at the specific time and frequency;

recording the location (time and frequency) and magnitude of this peak, helping to identify the specific feature or anomaly of the signal;

analyzing how the frequency components change over time, focusing on how the frequency components increase, decrease or remain stable over time, and identifying any sudden change or irregular pattern in frequency, which may indicate the abnormal state of the yarn.

Through the above steps, a variety of effective time-frequency features can be extracted from the laser signal as laser features.

In a possible implementation, S240 of using the yarn-out state detection model to obtain the yarn-out state of the target yarn path according to the image feature and the laser feature further includes the steps of:

S241: obtaining a yarn-out state feature of the target yarn path by fusing the image feature and the laser feature.

S242: using the yarn-out state detection model to obtain the yarn-out state of the target yarn path according to the yarn-out state feature.

In the embodiment of the present disclosure, the image feature and the laser feature are integrated by the data fusion technology to integrate the data sets from two different sources, and the two sets of features can be combined into a single feature vector. The yarn-out state detection model is pre-trained, and various state categories of the yarn state are identified by training the machine learning model. A certain amount of yarn path image data is required to train the model. The trained yarn-out state detection model can quickly and accurately identify the yarn state, and can also maintain high accuracy even under complex or changing conditions.

The main types of yarns involved in the solution of the embodiment of the present disclosure may include one or more of Partially Oriented Yarns (POY), Fully Drawn Yarns (FDY), Draw Textured Yarns (DTY) (or called low-elastic yarns), etc. For example, the types of yarns may specifically include Polyester Partially Oriented Yarns, Polyester Fully Drawn Yarns, Polyester Drawn Yarns, Polyester Draw Textured Yarns, etc.

Figure 4:
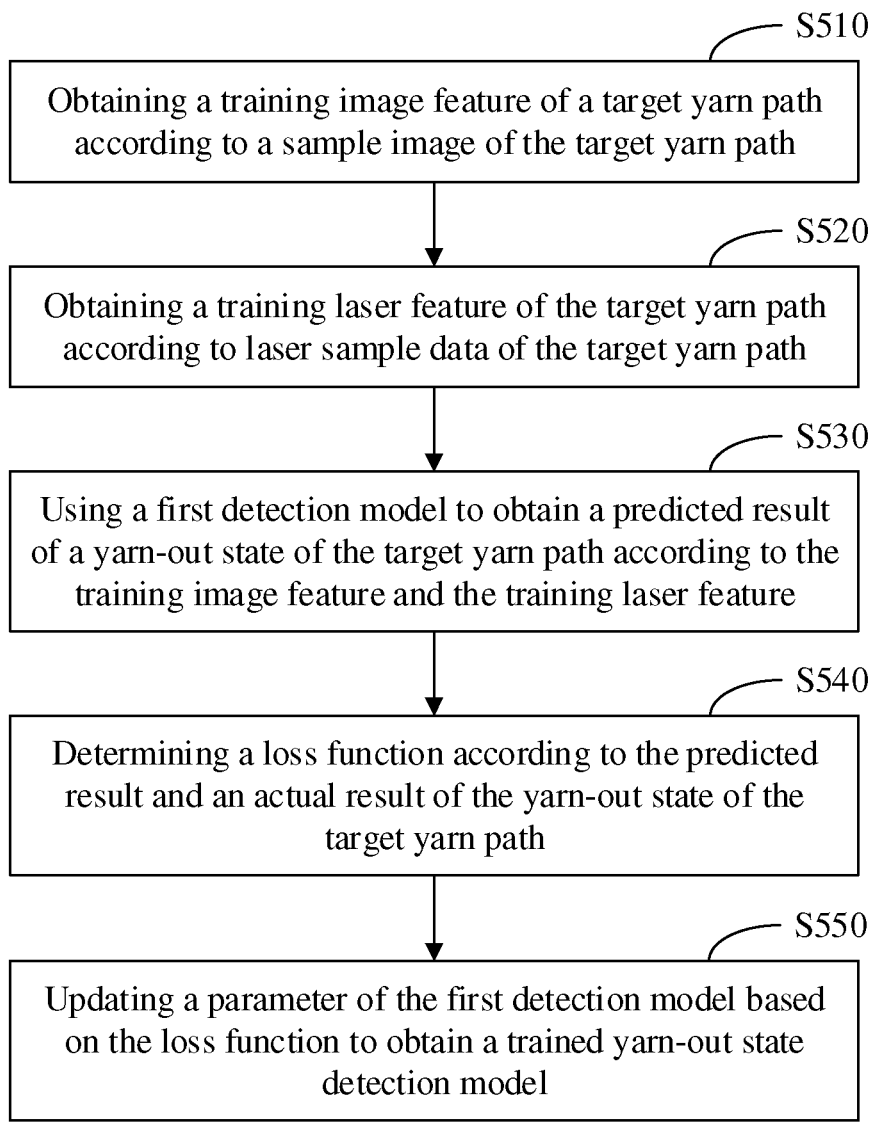
FIG. 4 is a schematic flowchart of a method for training a yarn-out state detection model according to an embodiment of the present disclosure.

The present disclosure further provides a method for training a yarn-out state detection model. FIG. 4 is a schematic flow chart of the method for training the yarn-out state detection model. As shown in FIG. 4, the method includes:

S510: obtaining a training image feature of a target yarn path according to a sample image of the target yarn path.

S520: obtaining a training laser feature of the target yarn path according to laser sample data of the target yarn path.

S530: using a first detection model to obtain a predicted result of a yarn-out state of the target yarn path according to the training image feature and the training laser feature.

S540: determining a loss function according to the predicted result and an actual result of the yarn-out state of the target yarn path.

S550: updating a parameter of the first detection model based on the loss function to obtain a trained yarn-out state detection model.

In one example, the structure of the first detection model includes:

an input layer that receives the processed image data and laser reflection data, where the above-mentioned data may need to be properly transformed and standardized to adapt to the network input;

convolutional layers that may effectively extract spatial features in images, where each convolutional layer extracts features at different levels through a set of learnable filters, and an activation function such as ReLU is used to increase the nonlinearity of the network;

a pooling layer, where the pooling layer (such as a maximum pooling layer) is added after the convolutional layers to reduce the spatial size of a feature map, thereby reducing the number of parameters and the amount of computation;

a fusion layer that is arranged after convolution and pooling to combine features from images and laser data, which can be achieved through splicing or other fusion techniques;

a fully connected layer, where one or more fully connected layers are used at the end of the network to integrate the previously extracted features, and the network model learns how to classify based on the extracted features in the fully connected layers; and an output layer that uses the softmax activation function to provide the probability distribution of multiple state levels, where the output of each neuron represents the probability that the yarn is at a particular state level.

In a possible implementation, the sample image and the laser sample data of the target yarn path may be pre-collected and manually annotated, or may be a conventional image and the laser reflection data collected by the inspection equipment during the routine inspection. After the yarn breakage occurs in the winding machine or the yarn spindle is downgraded due to a quality problem found in the subsequent appearance inspection process, the corresponding image data and laser data collected during the retrospective inspection are used as the sample data with anomaly.

In a possible implementation, S510 of obtaining the image feature of the target yarn path according to the sample image includes:

performing morphological processing on the sample image to obtain a third image; and obtaining the training image feature of the target yarn path according to the third image.

In a possible implementation, the step of performing morphological processing on the sample image to obtain the third image includes:

using a first sliding window to traverse the sample image, and performing a dilation operation to obtain a dilated image during each slide;

using a second sliding window to traverse the sample image, and performing an erosion operation to obtain an eroded image during each slide; and obtaining the third image according to morphological gradients of the dilated image and the eroded image.

In a possible implementation, the step of obtaining the training image feature of the target yarn path according to the third image includes:

dividing the third image into a plurality of segments in a length direction of the target yarn path to obtain a plurality of sample sub-images;

performing feature extraction on the plurality of sample sub-images to obtain a plurality of sample sub-image features; and obtaining a first training image feature of the target yarn path according to the plurality of sample sub-image features and corresponding weight values.

In a possible implementation, the step of obtaining the first training image feature of the target yarn path according to the plurality of sample sub-image features and corresponding weight values includes:

determining weight values of the plurality of sample sub-images according to width values of yarn paths contained in the plurality of sample sub-images;

obtaining second training image features of the plurality of sample sub-images according to the weight values of the plurality of sample sub-images and the training image feature; and obtaining the training image feature of the target yarn path according to the second training image features of the plurality of sub-images.

In a possible implementation, S520 of obtaining the training laser feature of the target yarn path according to the laser sample data of the target yarn path includes:

performing short-time Fourier transform on the laser sample data to obtain a time-frequency representation result;

determining a time-frequency feature according to the time-frequency representation result; and obtaining the training laser feature of the target yarn path according to the time-frequency feature.

In a possible implementation, the step of obtaining the training laser feature of the target yarn path according to the time-frequency feature includes:

extracting a main frequency feature, an energy peak feature and a dynamic change feature from the time-frequency feature; and obtaining the training laser feature of the target yarn path according to the main frequency feature, the energy peak feature and the dynamic change feature.

In a possible implementation, S530 of using the first detection model to obtain the predicted result of the yarn-out state of the target yarn path according to the training image feature and the training laser feature includes:

obtaining a training state feature of the target yarn path by fusing the training image feature and the training laser feature; and using the first detection model to obtain the predicted result of the yarn-out state of the target yarn path according to the training state feature.

In a possible implementation, S540 of determining the loss function according to the predicted result and the actual result of the yarn-out state of the target yarn path includes:

using the first detection model to make a prediction for the input training image feature and training laser feature to output the probability of each yarn state in each iteration; and comparing the predicted result from the model with the actual yarn state (true label), and calculating a loss value according to the loss function.

For a multi-class classification problem, the cross-entropy loss function is usually used. The cross-entropy loss function can quantify the difference between the probability distribution predicted by the model and the true label.

In a possible implementation, S550 of updating the parameter of the first detection model based on the loss function to obtain the trained yarn-out state detection model includes:

dividing an entire training data set into a plurality of batches; and for each batch, using an optimizer to update the parameter of the model according to the gradient of the loss function.

Multiple epochs (the number of times the complete data set is traversed) are usually repeated in this process. The performance of the model is generally improved after each epoch.

The trained yarn-out state detection model can be obtained through the above process, and this model can predict the yarn state according to the image feature and the laser feature.

Figure 5:
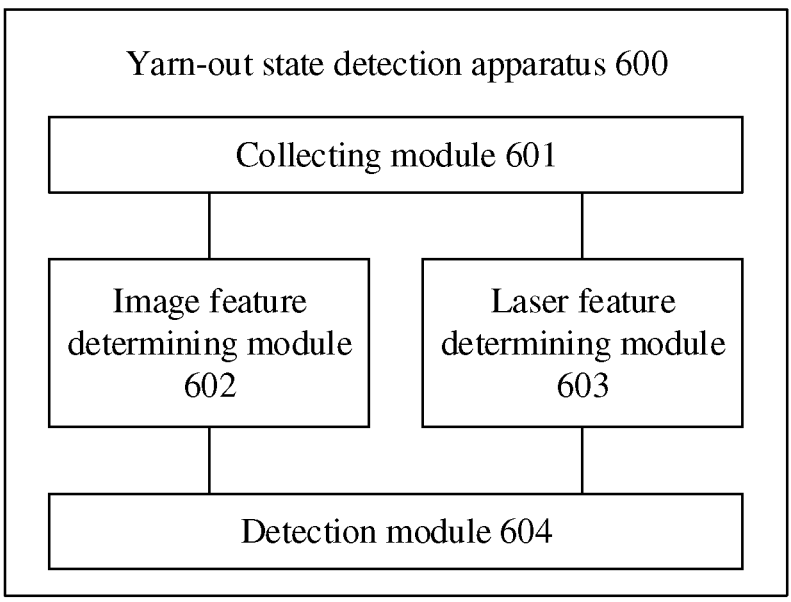
FIG. 5 is a structural schematic diagram of a yarn-out state detection apparatus according to an embodiment of the present disclosure.

FIG. 5 is a structural schematic diagram of a yarn-out state detection apparatus according to an embodiment of the present disclosure. As shown in FIG. 5, the apparatus at least includes:

a collecting module 601 configured to collect a first image and laser reflection data of a target yarn path in a spinning box;

an image feature determining module 602 configured to obtain an image feature of the target yarn path according to the first image;

a laser feature determining module 603 configured to obtain a laser feature of the target yarn path according to the laser reflection data; and a detection module 604 configured to use a yarn-out state detection model to obtain a yarn-out state of the target yarn path according to the image feature and the laser feature.

In a possible implementation, the collecting module 601 is configured to:

control an inspection equipment to move to be in front of a spinning box to be detected; and trigger a camera device and a laser scanning device of the inspection equipment to simultaneously collect the first image and the laser reflection data of the target yarn path in the spinning box, where the target yarn path includes a moving path formed by converging a plurality of yarn bundles ejected from a spinneret plate into one strand through a yarn guide hook.

In a possible implementation, the image feature determining module 602 is configured to:

perform morphological processing on the first image to obtain a second image; and obtain the image feature of the target yarn path according to the second image.

In a possible implementation, the image feature determining module 602 is configured to:

use a first sliding window to traverse the first image, and perform a dilation operation to obtain a dilated image during each slide;

use a second sliding window to traverse the first image, and perform an erosion operation to obtain an eroded image during each slide; and obtain the second image according to morphological gradients of the dilated image and the eroded image.

In a possible implementation, the image feature determining module 602 is configured to:

divide the second image into a plurality of segments in a length direction of the target yarn path to obtain a plurality of sub-images;

perform feature extraction on the plurality of sub-images to obtain a plurality of first image features; and obtain the image feature of the target yarn path according to the plurality of first image features and corresponding weight values.

In a possible implementation, the image feature determining module 602 is configured to:

determine weight values of the plurality of sub-images according to width values of yarn paths contained in the plurality of sub-images;

obtain second image features of the plurality of sub-images according to the weight values of the plurality of sub-images and the first image features; and obtain the image feature of the target yarn path according to the second image features of the plurality of sub-images.

In a possible implementation, the laser feature determining module 603 is configured to:

perform short-time Fourier transform on the laser reflection data to obtain a time-frequency representation result;

determine a time-frequency feature according to the time-frequency representation result; and obtain the laser feature of the target yarn path according to the time-frequency feature.

In a possible implementation, the laser feature determining module 603 is configured to:

extract a main frequency feature, an energy peak feature and a dynamic change feature from the time-frequency feature; and obtain the laser feature of the target yarn path according to the main frequency feature, the energy peak feature and the dynamic change feature.

In a possible implementation, the detection module 604 is configured to:

obtain a yarn-out state feature of the target yarn path by fusing the image feature and the laser feature; and use the yarn-out state detection model to obtain the yarn-out state of the target yarn path according to the yarn-out state feature.

For the description of specific functions and examples of the modules and sub-modules of the apparatus of the embodiment of the present disclosure, reference may be made to the relevant description of the corresponding steps in the above-mentioned method embodiments, and details are not repeated here.

Figure 6:
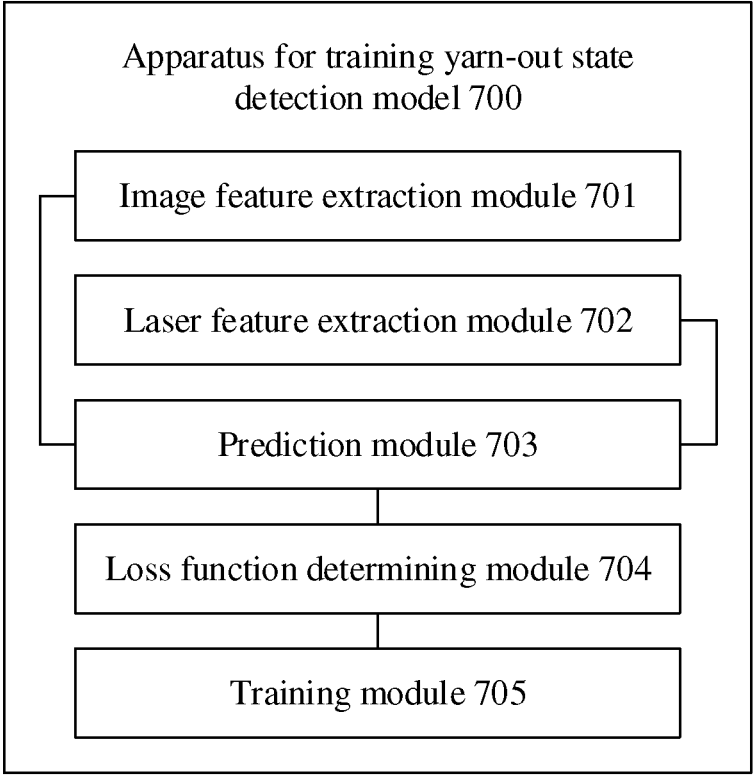
FIG. 6 is a structural schematic diagram of an apparatus for training a yarn-out state detection model according to an embodiment of the present disclosure.

FIG. 6 is a structural schematic diagram of an apparatus for training a yarn-out state detection model. As shown in FIG. 6, the apparatus includes:

an image feature extraction module 701 configured to obtain a training image feature of a target yarn path according to a sample image of the target yarn path;

a laser feature extraction module 702 configured to obtain a training laser feature of the target yarn path according to laser sample data of the target yarn path;

a prediction module 703 configured to use a first detection model to obtain a predicted result of a yarn-out state of the target yarn path according to the training image feature and the training laser feature;

a loss function determining module 704 configured to determine a loss function according to the predicted result and an actual result of the yarn-out state of the target yarn path; and a training module 705 configured to update a parameter of the first detection model based on the loss function to obtain a trained yarn-out state detection model.

For the description of specific functions and examples of the modules and sub-modules of the apparatus of the embodiment of the present disclosure, reference may be made to the relevant description of the corresponding steps in the above-mentioned method embodiments, and details are not repeated here.

Figure 7:
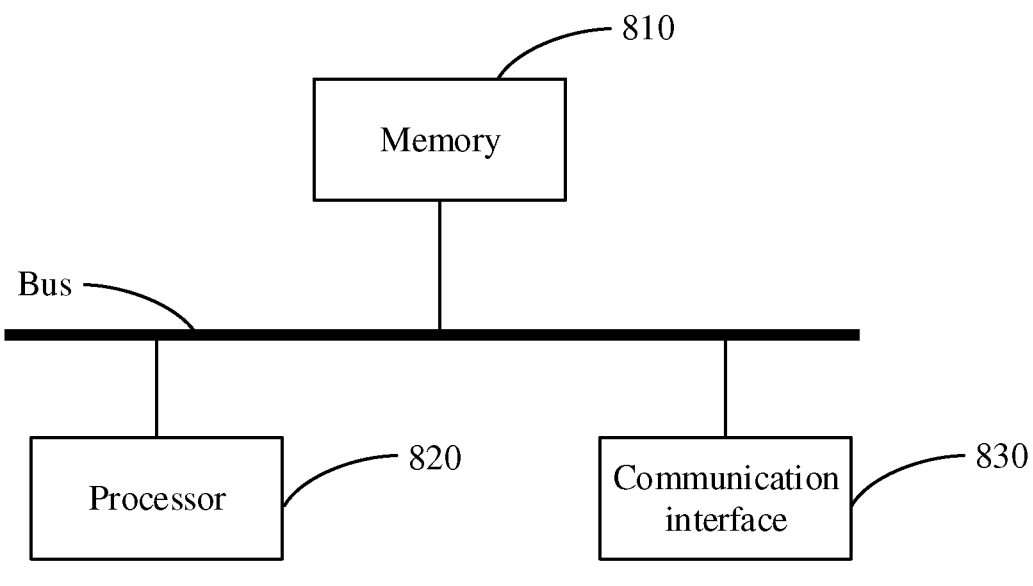
FIG. 7 is a block diagram of an electronic device for implementing the method of the embodiment of the present disclosure.

FIG. 7 is a structural block diagram of an electronic device according to an embodiment of the present disclosure. As shown in FIG. 7, the electronic device includes: a memory 810 and a processor 820, and the memory 810 stores a computer program that can run on the processor 820.

There may be one or more memories 810 and processors 820. The memory 810 may store one or more computer programs, and the one or more computer programs cause the electronic device to perform the method provided in the above method embodiment, when executed by the electronic device. The electronic device may also include: a communication interface 830 configured to communicate with an external device for data interactive transmission.

If the memory 810, the processor 820 and the communication interface 830 are implemented independently, the memory 810, the processor 820 and the communication interface 830 may be connected to each other and complete communication with each other through a bus. The bus may be an Industry Standard Architecture (ISA) bus, a Peripheral Component Interconnect (PCI) bus, or an Extended Industry Standard Architecture (EISA) bus, etc. The bus may be divided into address bus, data bus, control bus, etc. For ease of representation, the bus is represented by only one thick line in FIG. 7, but this thick line does not represent only one bus or only one type of bus.

Optionally, in a specific implementation, if the memory 810, the processor 820 and the communication interface 830 are integrated on one chip, the memory 810, the processor 820 and the communication interface 830 may communicate with each other through an internal interface.

It should be understood that the above-mentioned processor may be a Central Processing Unit (CPU) or other general-purpose processor, a Digital Signal Processor (DSP), an Application Specific Integrated Circuit (ASIC), a Field Programmable Gate Array (FPGA) or other programmable logic device, a discrete gate or transistor logic device, a discrete hardware component, etc. The general-purpose processor may be a microprocessor or any conventional processor, etc. It is worth noting that the processor may be a processor that supports the Advanced RISC Machines (ARM) architecture.

Further, optionally, the above-mentioned memory may include a read-only memory and a random access memory, and may also include a non-volatile random access memory. The memory may be a volatile memory or a non-volatile memory, or may include both a volatile memory and a non-volatile memory. Here, the non-volatile memory may include a Read-Only Memory (ROM), a Programmable ROM (PROM), an Erasable PROM (EPROM), an Electrically EPROM (EEPROM) or a flash memory. The volatile memory may include a Random Access Memory (RAM), which acts as an external cache. By way of illustration and not limitation, many forms of RAMs are available, for example, Static RAM (SRAM), Dynamic Random Access Memory (DRAM), Synchronous DRAM (SDRAM), Double Data Date SDRAM (DDR SDRAM), Enhanced SDRAM (ESDRAM), Synchlink DRAM (SLDRAM) and Direct RAMBUS RAM (DR RAM).

The above embodiments may be implemented in whole or in part by software, hardware, firmware or any combination thereof. When implemented by software, they may be implemented in the form of a computer program product in whole or in part. The computer program product includes one or more computer instructions. When the computer instructions are loaded and executed on a computer, the processes or functions described in the embodiments of the present disclosure are generated in whole or in part. The computer may be a general-purpose computer, a special-purpose computer, a computer network, or other programmable device. The computer instructions may be stored in a computer readable storage medium or transmitted from a computer readable storage medium to another computer readable storage medium. For example, the computer instructions may be transmitted from a website, computer, server or data center to another website, computer, server or data center in a wired (e.g., coaxial cable, optical fiber, Digital Subscriber Line (DSL)) or wireless (e.g., infrared, Bluetooth, microwave, etc.) way. The computer readable storage medium may be any available medium that can be accessed by a computer, or a data storage device such as server or data center that is integrated with one or more available media. The available media may be magnetic media (for example, floppy disk, hard disk, magnetic tape), optical media (for example, Digital Versatile Disc (DVD)), or semiconductor media (for example, Solid State Disk (SSD)), etc. It is worth noting that the computer readable storage medium mentioned in the present disclosure may be a non-volatile storage medium, in other words, may be a non-transitory storage medium.

Those having ordinary skill in the art can understand that all or some of the steps for implementing the above embodiments may be completed by hardware, or may be completed by instructing related hardware through a program. The program may be stored in a computer readable storage medium. The above-mentioned storage medium may be a read-only memory, a magnetic disk or an optical disk, etc.

In the description of the embodiments of the present disclosure, the description with reference to the terms "one embodiment", "some embodiments", "example", "specific example" or "some examples", etc. means that specific features, structures, materials or characteristics described in conjunction with the embodiment or example are included in at least one embodiment or example of the present disclosure. Moreover, the specific features, structures, materials or characteristics described may be combined in a suitable manner in any one or more embodiments or examples. In addition, those skilled in the art can integrate and combine different embodiments or examples and features of different embodiments or examples described in this specification without conflicting with each other.

In the description of the embodiments of the present disclosure, "/" represents or, unless otherwise specified. For example, A/B may represent A or B. The term "and/or" herein only describes an association relation of associated objects, which indicates that there may be three kinds of relations, for example, A and/or B may indicate that only A exists, or both A and B exist, or only B exists.

In the description of the embodiments of the present disclosure, the terms "first" and "second" are only for purpose of description, and cannot be construed to indicate or imply the relative importance or implicitly point out the number of technical features indicated. Therefore, the feature defined with "first" or "second" may explicitly or implicitly include one or more features. In the description of the embodiments of the present disclosure, "multiple" means two or more, unless otherwise specified.

The above descriptions are only exemplary embodiments of the present disclosure and not intended to limit the present disclosure. Any modifications, equivalent replacements, improvements and others made within the spirit and principle of the present disclosure shall be contained in the protection scope of the present disclosure.

What is claimed is:

1. A yarn-out state detection method, comprising:
   collecting a first image and a laser reflection data of a target yarn path in a spinning box;
   performing morphological processing on the first image, to obtain a second image;

dividing the second image into a plurality of segments in a length direction of the target yarn path, to obtain a plurality of sub-images;
   performing feature extraction on the plurality of sub-images, to obtain a plurality of first image features;
   obtaining an image feature of the target yarn path, according to the plurality of first image features and corresponding weight values, wherein the weight values are determined according to width values of yarn paths in the plurality of sub-images;
   performing short-time Fourier transform on the laser reflection data, to obtain a time-frequency representation result;
   determining a time-frequency feature, according to the time-frequency representation result;
   obtaining a laser feature of the target yarn path, according to the time-frequency feature; and
   using a yarn-out state detection model, to obtain a state category of the target yarn path according to the image feature and the laser feature.

2. The method of claim 1, wherein the collecting of the first image and the laser reflection data of the target yarn path in the spinning box, comprises:
   controlling an inspection equipment to move to be in front of a spinning box to be detected; and
   triggering a camera device and a laser scanning device of the inspection equipment to simultaneously collect the first image and the laser reflection data of the target yarn path in the spinning box, wherein the target yarn path comprises a moving path formed by converging a plurality of yarn bundles ejected from a spinneret plate into one strand through a yarn guide hook.

3. The method of claim 1, wherein the performing of morphological processing on the first image, to obtain the second image, comprises:
   using a first sliding window to traverse the first image, and performing a dilation operation to obtain a dilated image during each slide;
   using a second sliding window to traverse the first image, and performing an erosion operation to obtain an eroded image during each slide; and
   obtaining the second image according to morphological gradients of the dilated image and the eroded image.

4. The method of claim 1, wherein the obtaining of the image feature of the target yarn path, according to the plurality of first image features and corresponding weight values, comprises:
   determining weight values of the plurality of sub-images according to width values of yarn paths contained in the plurality of sub-images;
   obtaining second image features of the plurality of sub-images according to the weight values of the plurality of sub-images and the first image features; and
   obtaining the image feature of the target yarn path according to the second image features of the plurality of sub-images.

5. The method of claim 1, wherein the obtaining of the laser feature of the target yarn path, according to the time-frequency feature, comprises:
   extracting a main frequency feature, an energy peak feature and a dynamic change feature from the time-frequency feature; and
   obtaining the laser feature of the target yarn path according to the main frequency feature, the energy peak feature and the dynamic change feature.

6. The method of claim 1, wherein the using of the yarn-out state detection model, to obtain a yarn-out state of the target yarn path according to the image feature and the laser feature, comprises:

obtaining a yarn-out state feature of the target yarn path by fusing the image feature and the laser feature; and using the yarn-out state detection model to obtain the yarn-out state of the target yarn path according to the yarn-out state feature.

7. A method for training a yarn-out state detection model, comprising:

performing morphological processing on a sample image, to obtain a third image;

dividing the third image into a plurality of segments in a length direction of a target yarn path, to obtain a plurality of sample sub-images;

performing feature extraction on the plurality of sample sub-images, to obtain a plurality of sample sub-image features;

obtaining a training image feature of the target yarn path, according to the plurality of sample sub-image features and corresponding weight values, wherein the weight values are determined according to width values of yarn paths in the plurality of sample sub-images;

performing short-time Fourier transform on laser sample data, to obtain a time-frequency representation result;

determining a time-frequency feature, according to the time-frequency representation result;

obtaining a training laser feature of the target yarn path, according to the time-frequency feature;

using a first detection model, to obtain a predicted result of a state category of the target yarn path according to the training image feature and the training laser feature;

determining a loss function according to the predicted result and an actual result of the state category of the target yarn path; and updating a parameter of the first detection model based on the loss function to obtain a trained yarn-out state detection model.

* * * * *